United States Patent [19]

Nakao et al.

[11] 4,440,134

[45] Apr. 3, 1984

[54] FUEL INJECTION SYSTEM FOR INTERNAL COMBUSTION ENGINES

[75] Inventors: Kiyoharu Nakao, Isehara; Fumihide Sato, Yokohama, both of Japan

[73] Assignee: Kabushiki Kaisha Komatsu Seisakusho, Tokyo, Japan

[21] Appl. No.: 378,180

[22] Filed: May 14, 1982

[30] Foreign Application Priority Data

| | | | |
|---|---|---|---|
| May 15, 1981 | [JP] | Japan | 56-73114 |
| Jun. 17, 1981 | [JP] | Japan | 56-87919 |
| Jun. 17, 1981 | [JP] | Japan | 56-87923 |
| Jun. 22, 1981 | [JP] | Japan | 56-90811 |

[51] Int. Cl.³ .......................... F02M 47/02
[52] U.S. Cl. .................. 123/447; 417/462; 417/540; 123/450; 123/458
[58] Field of Search ............... 123/447, 446, 450, 458, 123/467; 417/462, 253, 294, 299, 300, 540, 542, 543

[56] References Cited

U.S. PATENT DOCUMENTS

| | | | |
|---|---|---|---|
| 3,412,718 | 11/1968 | Long | 123/447 |
| 3,592,568 | 7/1971 | Fenne | 417/540 |
| 3,810,581 | 5/1974 | Rhine | 123/450 |
| 3,891,151 | 6/1975 | Showalter | 123/447 |
| 4,184,459 | 1/1980 | Ishii et al. | |
| 4,325,340 | 4/1982 | O'Neill | 123/447 |
| 4,348,998 | 9/1982 | Stumpp | 123/447 |
| 4,392,791 | 7/1983 | Mandroian | 417/540 |

FOREIGN PATENT DOCUMENTS 55-29250 8/1980 Japan.

Primary Examiner—Charles J. Myhre
Assistant Examiner—Carl Stuart Miller
Attorney, Agent, or Firm—Armstrong, Nikaido, Marmelstein & Kubovcik

[57] ABSTRACT

A fuel injection system for an internal combustion engine employing a rotary valve for delivering fuel to fuel injectors in which fuel injection timing is precisely controlled to an optimum range by automatically controlling the rotary valve in response to the number of revolutions of the engine. The system includes a high pressure accumulator connected to a fuel pump and a low pressure accumulator connected to a tank through a variable restrictor valve. The rotary valve functions to selectively connect each injector to the high and low pressure accumulators as it rotates whereby metered amount of fuel can be fed into a plunger chamber of each injector when a piston chamber of the injector is connected to the low pressure accumulator and the fuel can be injected through nozzle orifices when the piston chamber is connected to the high pressure accumulator.

10 Claims, 12 Drawing Figures

FUEL INJECTION SYSTEM FOR INTERNAL COMBUSTION ENGINES

BACKGROUND OF THE INVENTION

This invention relates to a fuel injection system for internal combustion engines.

In a conventional fuel injection system of diesel engines, the shaft of the fuel injection pump is connected through a coupling and an automatic timer to the cam shaft of the engine and the fuel from the fuel tank is supplied under pressure into each injector at a predetermined timing in proportion to the number of revolutions of the engine. In the process of delivery of fuel under pressure by the injection pump, when the fuel under high pressure to be supplied into each injector has reached a pressure more than that required to open the needle valve of each injector, the needle valve is lifted to inject fuel into each cylinder.

The amount of injection of fuel varies depending on the amount of forward movement of the control rack provided in the injection pump. The amount of forward movement of the control rack is controlled by a flywheel connected to the shaft of the injection pump through a linkage. The arrangement is made such that the control rack controls the effective stroke of the piston of a jerk pump of the injection pump in proportion to its forward movement thereby controlling the amount of injection of fuel.

Further, the fuel injection timing can be altered by means of the automatic timer in proportion to the revolving speed of the engine. In brief, the arrangement is made such that the injection timing is advanced as the revolving speed of the engine increases.

In such a conventional fuel injection system, however, because each piston for delivering fuel under pressure is driven by the cam mounted on the shaft of the injection pump, the fuel injection pressure in the low revolution range of the engine will become low and therefore the fuel injection in the low revolution range will become unstable causing deviation in the amount of injection of fuel and improper atomization of fuel injected into each cylinder thereby rendering it difficult to rotate the engine smoothly.

Further, the fuel injection timing can be represented as a function of the revolving speed of the engine; however, at the present time the correction of the injection timing to cope with the exhaust gas emission control and the correction thereof in proportion to the amount of injection of fuel are not made at all. Therefore, it is impossible for the above-mentioned fuel injection system to cope with the exhaust gas emission control, the noise control and the improvement of fuel combustion efficiency all of which are expected to become more and more severe in the future.

SUMMARY OF THE INVENTION

It is therefore an object of the present invention to provide a fuel injection system for an internal combustion engine which overcomes the above noted problems of the prior art.

Another object of the present invention is to provide a fuel injection system for an internal combustion engine which can provide a stable and uniform fuel injection throughout a wide range of engine speed.

A further object of the present invention is to provide a fuel injection system for an internal combustion engine wherein fuel injection timing and amount of fuel to be injected can be varied to obtain an optimum combustion.

In accordance with an aspect of the present invention, there is provided a fuel injection system for an internal combustion engine having at least one cylinder and a cam shaft operatively associated therewith, comprising: a fuel pump driven by said engine for delivering fuel; first accumulator means for receiving and storing the fuel from said fuel pump; rotary valve means having an inlet port connected with said first accumulator means, at least one outlet port and a drain port, said rotary valve means comprising a housing, a sleeve mounted for rotation within said housing, said sleeve having at least one opening formed therein and rotary shaft means mounted for rotation within said sleeve, said rotary shaft means being rotated in synchronism with said cam shaft and having means for selectively connecting the outlet port with the inlet port and the drain port; means for automatically controlling position of said sleeve relative to said housing in response to number of revolutions of the engine; second accumulator means connected at one end with the drain port of said rotary valve means and at the other end with a tank; variable restrictor valve means disposed between said second accumulator means and said tank; means for automatically controlling degree of opening of said variable restrictor valve means in response to fluid pressure in said second accumulator means; and at least one injector means connected with the outlet port of said rotary valve means for injecting the fuel into said cylinder.

The above and other objects, features and advantages of the present invention and the manner of attaining them will become more apparent and understandable from the following description, which is to be read in conjunction with the accompanying drawings showing some preferred embodiments of the invention.

DESCRIPTION OF THE PREFERRED EMBODIMENTS

The present invention will now be described in detail below by way of example only with reference to the accompanying drawings.

Figure 1:
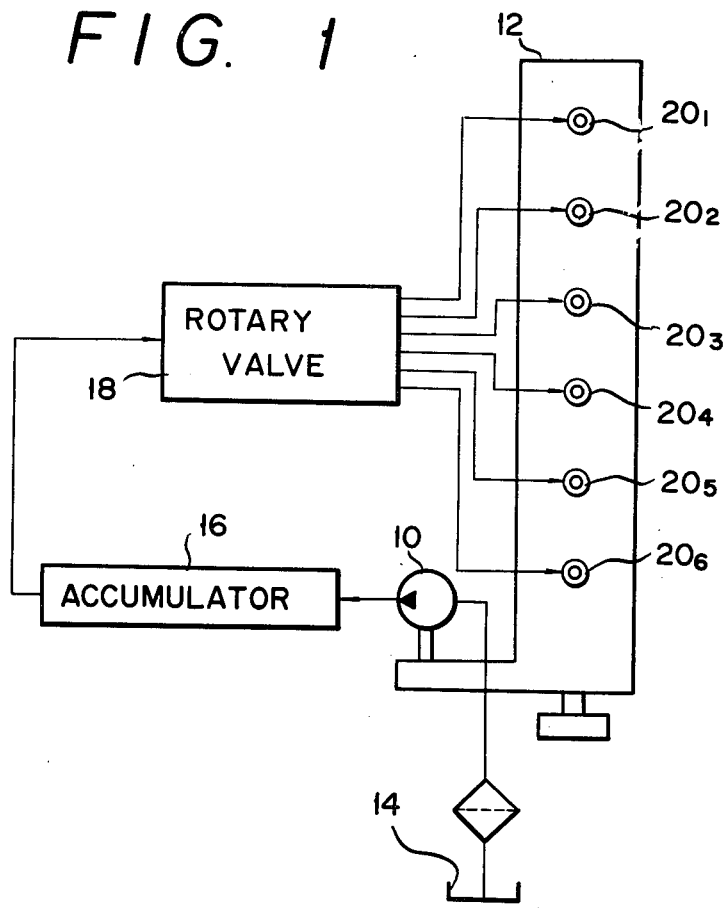
FIG. 1 is a schematic representation of a fuel injection system according to the present invention.

FIG. 1 is a schematic explanatory view of the present invention. Reference numeral 10 denotes a high pressure pump arranged to be driven by an engine 12 so as to deliver the fuel from a fuel tank 14 at a high pressure. The fuel under a high pressure delivered by the high pressure pump 10 is pulsating with a large pressure fluctuation. Therefore, the fuel delivered from the high pressure pump 10 is once stored in a high pressure accumulator 16 to thereby reduce the pressure fluctuation and then is supplied into a rotary valve 18. The rotary valve 18 is arranged to be driven in synchronism with a cam shaft of the engine 12 so as to dispense or supply the fuel under a high pressure from the accumulator 16 into fuel injectors $20_1$ to $20_6$.

Figure 2:
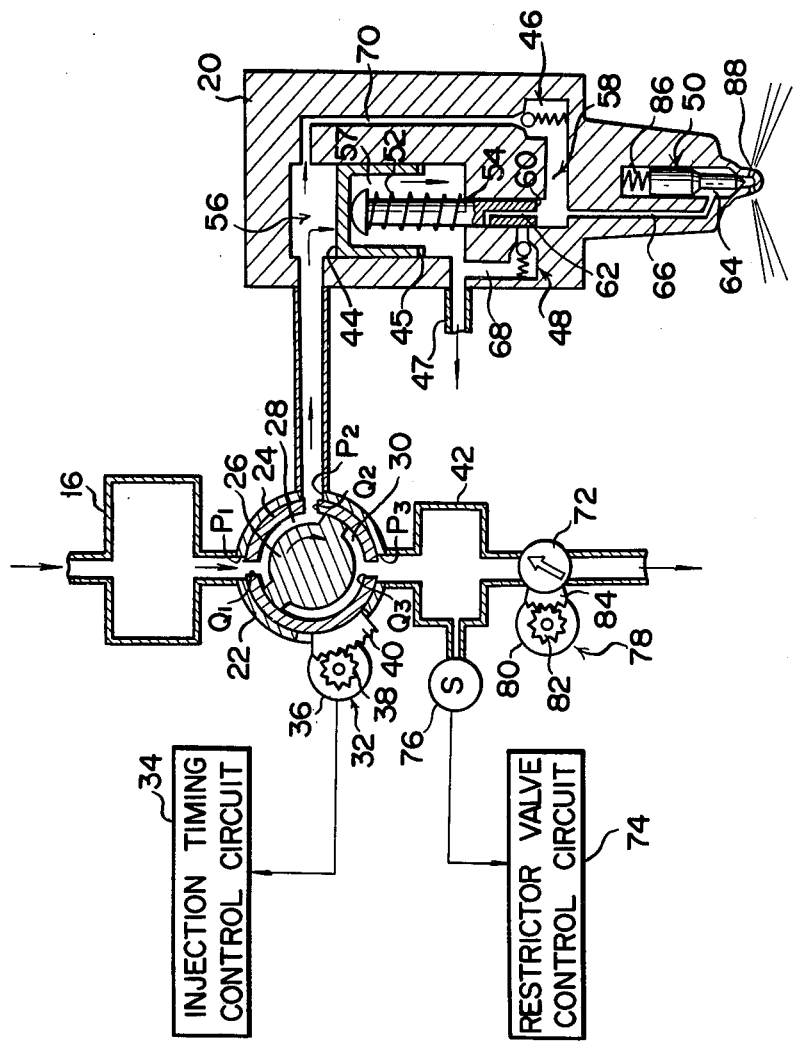
FIG. 2 is a sectional view of prime parts of the fuel injection system according to the present invention.

The rotary valve 18 comprises, as shown in FIG. 2, a housing 22, a cylindrical rotary sleeve 24 disposed in sliding contact with the inner surface of the housing so that it may be turned freely for a predetermined angle, and a rotary shaft 26 disposed concentrically and in sliding contact with the inner surface of the rotary sleeve 24 so that it may be rotated freely. The housing 22 and the rotary sleeve 24 has ports $P_1$ to $P_3$, $Q_1$ to $Q_3$, respectively, formed in predetermined opposite positions. The rotary shaft 26 has circumferentially extending recesses 28 and 30 formed in predetermined position in the outer peripheral part thereof. These recesses 28 and 30 serve to switch over an injection area and a metering area (which is a zone to set the amount of fuel injection). The rotary shaft 26 is adapted to be driven in synchronism with a cam shaft (not shown) of the engine in a predetermined direction, for example, in a clockwise direction.

A rotary sleeve drive means 32 is provided which serves to control the fuel injection timing and is adapted to turn the rotary sleeve 24 for a predetermined angle in a clockwise or counterclockwise direction in response to a control signal transmitted from an injection timing control circuit 34 to thereby change the positions of ports $Q_1$ to $Q_3$ relative to those of ports $P_1$ to $P_3$. This injection timing control circuit 34 is arranged to generate a rotary sleeve position control signal as an output in response to a speed signal derived from an engine revolving speed detector (not shown). The rotary sleeve drive means 32 is adapted to turn the rotary sleeve 24 by, for example, a motor 36 through gears 38 and 40. The ports $P_1$, $P_2$ and $P_3$ of the housing 22 are connected to the accumulator 16, the injector 20 and a low pressure accumulator 42, respectively.

The injector 20 comprises a booster piston 44, a check valve 46, a suction valve 48 and a needle valve 50. The booster piston 44 serves to increase or multiply the pressure of the fuel supplied therein by the rotary valve 18 about seven or eight times and control the amount of fuel to be injected. The booster piston 44 has a radially extending slit 45 formed in the lower end thereof and correspondingly to a drain passage 47, the slit 45 being arranged to communicate with the drain passage 47 when the piston 44 is moved to and around the stroke end. The booster piston 44 is arranged to be urged towards the side of a piston chamber 56 by the resilient force of a return spring 52 through a piston plunger 54. The pressure intensification ratio of the booster piston 44 is determined by the ratio of the cross-sectional area of piston 44 to that of plunger 54. The volume of a plunger chamber 58 is determined by the position where the back pressure (which is the pressure on the side of the piston chamber 56) has been brought in equilibrium with the compressive force (or urging force) of the return spring 52, thereby determining the amount of fuel injection.

Stating in more detail, if the back pressure of the piston 44 is raised, the piston plunger 54 will move downwards so as to reduce the volume of the plunger chamber 58 thereby reducing the amount of fuel injection. Reversely, if the back pressure is reduced, the piston plunger 54 will naturally move upwards so as to increase the volume of the plunger chamber 58 thereby increasing the amount of fuel injection. The adjustments of the amount of fuel injection may be made in the above-mentioned manner.

The piston plunger 54 has a passage 62 formed therein which communicates its lower end face 60 and its side face. The arrangement is made such that, when the lower end face 60 has reached in the vicinity of the bottom surface of the plunger chamber 58, a fuel passage 66 extending from the plunger chamber 58 to nozzle chamber 64 and the plunger chamber 58 itself are allowed to communicate with the suction valve 48. This suction valve 48 serves to prevent the after drip or secondary injection of fuel, and is adapted, after the fuel injection, to suck or draw back the fuel within both the passage 66 and the nozzle chamber 64 through the passage 62 of the piston plunger 54 into the passage 68 and to thereby reduce the fuel pressure. The passage 68 is connected to a drain tank (not shown) through the drain passage 47.

The check valve 46 allows to introduce the fuel in the piston chamber 56 into the plunger chamber 58.

The low pressure accumulator 42 serves to vary the back pressure of the booster piston 44, and the arrangement is made so that the back pressure of the booster piston 44 will vary depending on the pressure of the low pressure accumulator 42. In brief, the back pressure will increase if the pressure within the low pressure accumulator 42 is raised, while it will decrease if the pressure in the low pressure accumulator is lowered. This low pressure accumulator 42 is connected through a variable restrictor valve 72 to the drain tank. A restrictor valve control circuit 74 is provided which serves to drive a restrictor valve drive means 78 in proportion to the value of deviation between the pressure within the low pressure accumulator 42 detected by a pressure sensor 76 and a preset pressure so as to control the degree of opening of the restrictor valve 72 thereby adjusting the pressure inside the accumulator 42 at a preset value. This restrictor valve drive means 78 is arranged, in the similar manner to the case of the above-mentioned drive means 32, to control the restrictor valve 72 by means of a motor 80 through gears 82, 84.

Now, the fuel under a high pressure discharged by the high pressure pump 10 (FIG. 1) is once stored in the high pressure accumulator 16. When the rotary shaft 26 occupies the position as shown in FIG. 2, the fuel under a high pressure will flow from the high pressure accumulator 16 through ports $P_1$, $Q_1$, recess 28, ports $Q_2$, $P_2$ of the rotary valve 18 into the piston chamber 56 of the injector 20, whereby pushing down the piston 44 against the biasing force of the return spring 52. Along with the downward movement of the piston 44, the piston plunger 54 is moved downwards with its lower end face 60 compressing the fuel within the plunger chamber 58, the passage 66 and the nozzle chamber 64. The compressive force available at that time is increased in proportion to the aforementioned pressure intensification or multification ratio of the fuel pressure exerted on the piston 44 thus giving an extremely high pressure.

With increase in the fuel pressure within the passage 66 and the nozzle chamber 64, the needle valve 50 will be lifted against the force of a spring 86 thus injecting fuel through nozzle orifices 88. This fuel injection will continue until the booster piston 44 reaches its stroke end.

As the booster piston 44 approaches its stroke end, the passage 47 leading to the drain port is restricted by the slit 45 formed in the lower end of the piston 44 so that the piston 44 may reach its stroke end while it is being subjected to the buffer or shock absorbing action provided by the restriction of the drain port passage. When the booster piston 44 has reached its stroke end, a lower end piston chamber 57 is allowed to communicate through the slit 45 with the drain passage 47 and consequently fuel may not be confined within the lower end piston chamber 57. Therefore, the speed decrease of the booster piston 44 near its stroke end will be constrained in the speed drop range due to the aforementioned buffer action, and so there is no possibility of causing unnecessary drop in the piston speed.

In the foregoing embodiment, there is shown and described an example wherein the booster piston 44 is formed with the slit 45; however, this means is not to be limited to the slit, a small orifice may be used instead.

When the booster piston 44 has reached its stroke end, the passage 66 is allowed to communicate through the passage 62 of the plunger 54 with the suction valve 48 so that the fuel under a high pressure within the passage 66 may be sucked or drawn back through the suction valve 48 into the drain tank (not shown). As a result, the fuel pressure within the passage 66 and nozzle chamber 64 will rapidly reduce and hence the needle valve 50 will be pushed downward by the action of the spring 86 so as to block the nozzle orifices 88 thus finishing the fuel injection. The fuel pressure on the side of the nozzle orifices 88 after the injection will be lowered in this manner. The fuel sucking-back arrangement can prevent the occurrence of after-drip of fuel and secondary fuel injection due to hunting of the needle valve 50 thereby enabling a generally rectangular waveform of injection rate to be obtained.

Figure 3:
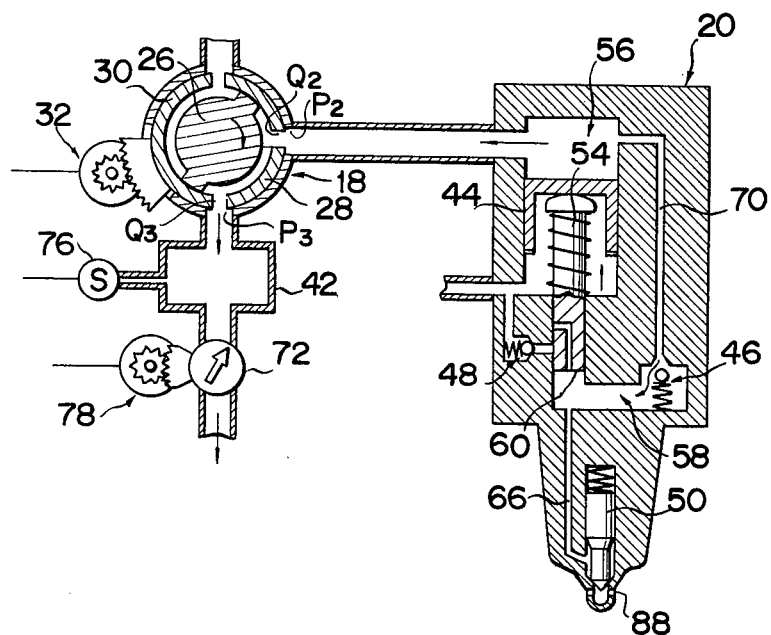
FIG. 3 is similar to FIG. 2 but showing a fuel injector being in fuel metering stage.

When, after the completion of fuel injection, the rotary shaft 26 is turned to the position as shown in FIG. 3, the piston chamber 56 of the injector 20 is allowed to communicate through ports $P_2$, $Q_2$, the recess 28 and ports $Q_3$, $P_3$, of the rotary valve 18 with the low pressure accumulator 42. In consequence, the fuel under a high pressure in the piston chamber 56 will flow into the low pressure accumulator 42 to ease the high fuel pressure exerted on the piston 44 so that the piston 44 and the plunger 54 may be moved upwards by the force of the return spring 52. Thus, the piston 44 will move up to a position where the back pressure set by the low pressure accumulator 42 is brought into equilibrium with the compressive force of the return spring 52.

With the upward movement of the plunger 54, the pressure within the plunger chamber 58 will be lowered thus opening the check valve 46. With the upward movement of the piston 44, the fuel within the piston chamber 56 will flow through the passage 70 and the check valve 46 into the plunger chamber 58 by an amount corresponding to the upward stroke of the plunger 54. Therefore, the volume corresponding to the upward displacement of the plunger 54 from the lowermost stroke end to the uppermost stroke end will correspond to the amount of injection of fuel per one stroke. If and when the pressure within the low pressure accumulator 42 and hence the back pressure of the piston 44 is changed, then the stroke of the piston 44 and the plunger 54 will change to thereby change the amount of fuel flow into the chamber 58 thus changing the amount of fuel injection. In brief, the amount of fuel injection can be varied to a desired value by adjusting the back pressure of the piston 44.

Upon the completion of the fuel injection, when the rotary shaft 26 is turned to the position as shown in FIG. 2, fuel under a high pressure is again supplied from the high pressure accumulator 16 into the injector 20 and so the booster piston 44 is pushed down to inject fuel through the nozzle orifices 88 as mentioned hereinabove. With the rotation of the rotary shaft 26 in synchronism with the cam shaft of the engine, the abovementioned operations will be made repeatedly thereby injecting fuel under high pressure through the nozzle orifices 88 of the injector 20.

Figure 4:
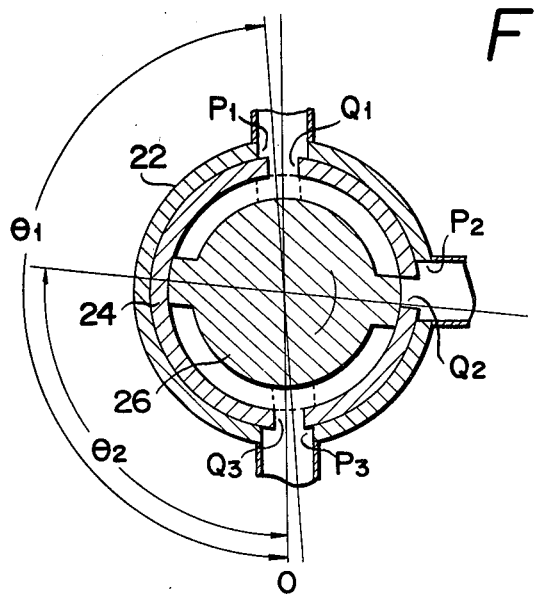
FIGS. 4 to 6 are sectional views of a rotary valve employed in the present invention showing how the fuel injection timing can be varied.

The injection timing of fuel from the injector 20 may be varied by changing the position of the rotary sleeve 24 with respect to the housing 22. As shown in FIG. 4, in the case where the ports $P_1$ to $P_3$ of the housing 22 are registered with the ports $Q_1$ to $Q_3$ of the rotary sleeve 24 (the position of the rotary sleeve 24 relative to the housing 22 at this situation is set to be reference point or zero), fuel is supplied into the chamber 56 while the rotary shaft 26 is rotated from angle $\theta_2$ to angle $\theta_1$, and the fuel injection is commenced when the angle of rotation of the rotary shaft 26 exceeds $\theta_2$.

Therefore, when it is desired to advance the fuel injection timing, it is only necessary to reduce the angle of rotation $\theta_2$ of the rotary shaft 26, while when it is desired to delay the injection timing, it is only required to increase the angle of rotation $\theta_2$.

Figure 5:
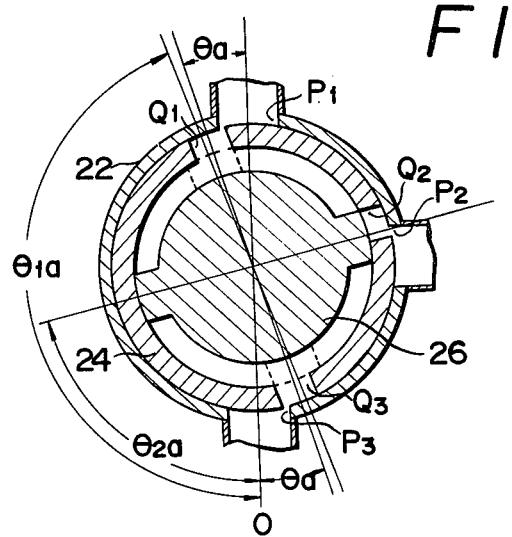

Now, when the injection timing of the injector is advanced, as shown in FIG. 5, the rotary sleeve 24 is turned by means of the rotary sleeve drive means 32 in the direction opposite to that of rotation of the rotary shaft 26 (that is; in the counterclockwise direction) by an angle $\theta a$ to shift the positions of the ports $Q_1$ to $Q_3$ of the rotary sleeve 24 relative to the ports $P_1$ to $P_3$ of the housing 22. By so doing, when the rotary shaft 26 has rotated through an angle $\theta_2 a (=\theta_2 - \theta a) < \theta_2$ (as shown by broken lines), the ports $P_1$ and $P_2$ will communicate with each other so that the injection timing may be advanced by the angle $\theta a$ as compared to the case of FIG. 4.

Figure 6:
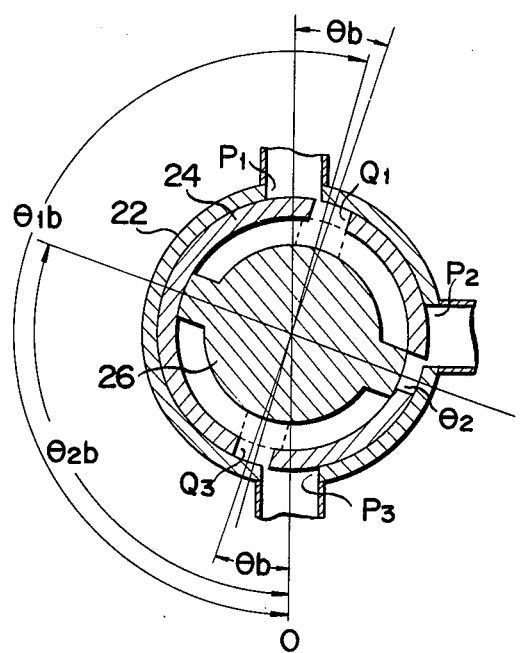

Reversely, when it is desired to delay the injection timing, as shown in FIG. 6, the rotary sleeve 24 is turned in the same direction as that of rotation of the rotary shaft 26 (that is; in the clockwise direction) thereby changing the positions of the ports $Q_1$ to $Q_3$ relative to those of the ports $P_1$ to $P_3$ as shown. By so doing, when the rotary shaft 26 has rotated through an angle $\theta_2 b \ (= \theta_2 + \theta b) > \theta_2$ (as shown by broken lines), the port $P_1$ will communicate with the port $P_2$. Therefore, the injection timing can be delayed by the angle $\theta b$ as compared to the case of FIG. 4. The rotary sleeve 24 can be rotated to an optimum position depending on the engine revolving speed under the control of the injection timing control circuit 34.

By thus rotating the rotary sleeve 24 by a desired angle in either counterclockwise or clockwise direction, the injection timing can be adjusted.

When the restrictor valve 72 is shut off, the pressure within the accumulator 42 becomes equal to that of the piston chamber 56 in the injector 20 so that the piston 44 remains to be subjected to the high pressure preventing the upward movement of the piston 44 after the fuel injection thereby ceasing the subsequent fuel injection.

In such a pressure intensifying unit injector, the arrangement is made such that the amount of metering is determined by the pressure prevailing in the low pressure accumulator 42 as mentioned above and the pressure within the low pressure accumulator 42 is electrically detected or sensed by the pressure sensor 76 and the variable restrictor valve 72 is electrically energized depending on the value detected by the sensor 76 thereby enabling the pressure within the low pressure accumulator 42 to be variably adjusted.

Figure 7:
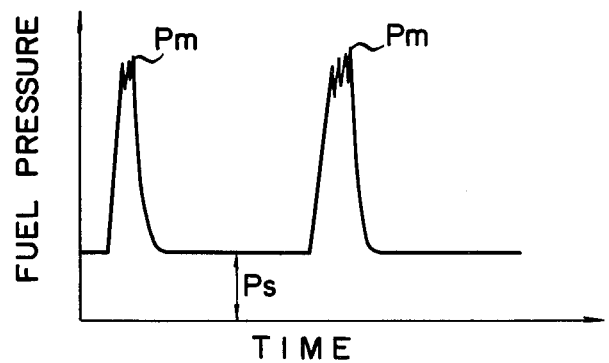
FIG. 7 is a graph plotting fuel pressure in a low pressure accumulator relative to time passed.

Further, in adjusting the pressure in the low pressure accumulator 42, the pressure varies as shown in FIG. 7. When the outlet ports P$_2$ and drain P$_3$ are allowed to communicate with each other, the pressure in the accumulator 42 will rise momentarily to a value of P$_m$ and then reduce to a pressure of P$_s$ set by the variable restrictor valve 72.

Figure 8:
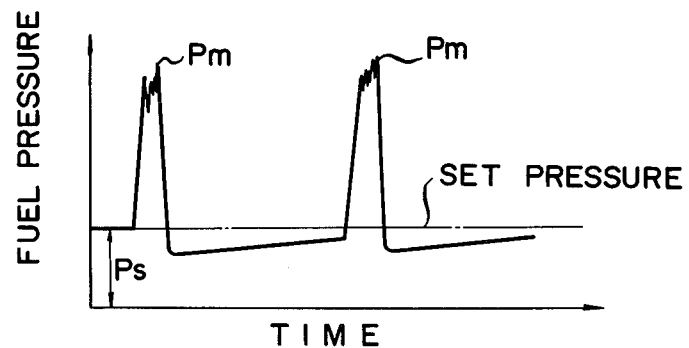
FIG. 8 is similar to FIG. 7 but showing a state in which the opening rate of a variable restrictor valve is increased to a large extent.

For this reason, in such a pressure adjusting arrangement, in the course of adjustment of the degree of opening of the variable restrictor valve 72 by means of the pressure sensor 76, if the sensor 76 senses a high value during the pressure fluctuation and opens the restrictor valve 72 wider than the normal degree of opening, the pressure available at the time of pressure adjustment will become lower than the set or desired value as shown in FIG. 8, causing a deficit in the amount of metering. In such a case, it is difficult to raise the pressure in the low pressure accumulator 42 to the set pressure, and so it is necessary to wait for the pressure supply during the next metering period.

Further, in case of effecting a quick deceleration of the engine, it is necessary to quickly raise the pressure within the low pressure accumulator 42. However, in the above-mentioned pressure adjusting arrangement, the adjustment pressure may be adjusted after the completion of one cycle for the deceleration instruction of the engine. This is because it is difficult to increase the pressure within the low pressure accumulator 42 from a low to a high pressure during one cycle.

For these reasons, in the above-mentioned embodiment of the pressure adjusting arrangement, there is a risk of causing a deterioration of the response of the engine and a deterioration of the stability thereof.

Figure 9:
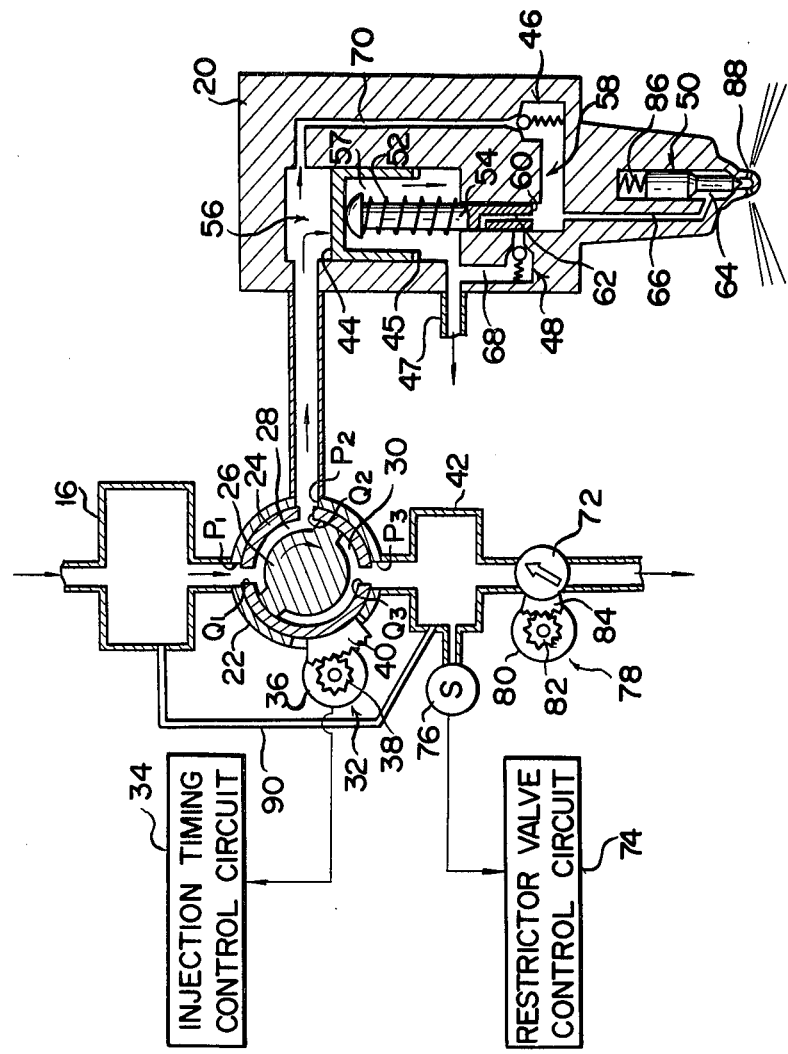
FIG. 9 is similar to FIG. 2 but showing another embodiment of the present invention.

Referring to FIG. 9, there is shown another embodiment of the fuel injection system of the present invention. In brief, in this embodiment, the high pressure accumulator 16 is connected through a passage 90 to the low pressure accumulator 42. Other configurations of this embodiment are entirely the same as those of FIG. 1. By such an arrangement, a small amount of stabilized fuel under high pressure from the high pressure accumulator 16 will flow into the low pressure accumulator 42, the pressure of which may be varied by turning the rotary valve 18, thereby enabling stabilization of the pressure within the low pressure accumulator 42 to be achieved. As a result, it is possible to adjust easily the pressure within the low pressure accumulator 42 and improve the response of the engine and the stability thereof.

Figure 10:
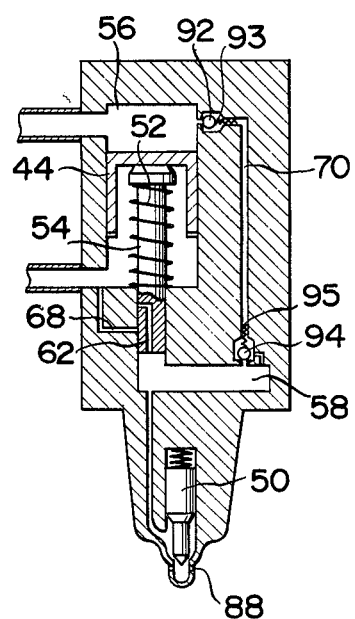
FIG. 10 is a sectional view of a modified fuel injector employed in the present invention.

Referring to FIG. 10, there is illustrated a further embodiment of a unit injector according to the fuel injection system of the present invention. In the embodiments of FIGS. 2 to 9, one normally closed check valve 46 is mounted between the piston chamber 56 and the plunger chamber 58. Whilst, in the embodiment of FIG. 10, two normal-open check valves 92 and 94 are mounted instead. By such an arrangement, it is possible to obtain a desired stable amount of metering at all times without any deviation.

The unit injector of FIG. 10 will now be described in detail below.

Disposed at one end of the fuel passage 70 on the side of the piston chamber 56 is a first normal-open check valve 92 adapted to block the passage 70 against the force of a spring 93 only when the fluid pressure within the piston chamber 56 reaches a value at which the piston is actuated. Disposed at the other end of the fuel passage 70 on the side of the plunger chamber 58 is a second normal-open check valve 94 adapted to close against the force of the spring 95 at the moment when the piston 44 begins its downward movement. The spring 93 should be adjusted to have a resilient force which, under a relatively low fluid pressure during the fuel metering, allows the check valve 92 to remain opened against the fluid pressure, whilst the spring 95 may be very weak in spring force.

The spring 95 of the check valve 94 may be omitted. Actually, by omitting the spring 95, the response of the check valve 94 when it is closed can be improved.

In the above-mentioned arrangement, during the fuel injection when the booster piston 44 is moved downwards by the fuel under high pressure exerted inside the piston chamber 56 against the biasing force of the return spring 52, the first check valve 92 is closed by the pressure exerted inside the piston chamber 56, whilst the second check valve 94 is closed by the pressure exerted inside the plunger chamber 58 at the time of fuel injection thereby allowing the fuel within the plunger chamber 58 to be injected through the nozzle orifices 88.

Upon the completion of the fuel injection stroke, the passage 62 formed in the plunger 54 will communicate with the passage 68 so that the pressure in the plunger chamber 58 will become low. At that time, the second check valve 94 becomes open, but the piston chamber 56 is still kept at the piston actuating pressure thus closing the first check valve 92. Therefore, even when the second check valve 94 is opened, the fuel inside the piston chamber 56 will not leak through the passages 62, 68 into drain passage 47.

Subsequently, when the rotary valve 18 is turned to reduce the pressure in the piston chamber 56, the booster piston 44 is returned to a raised position together with the plunger 54 by the action of the return spring 52.

At that time, the pressure within the piston chamber 56 and the plunger chamber 58 will be reduced so as to open the first and second check valves 92 and 94 so that, with the return movement of the plunger 54, the fuel within the piston chamber 56 may pass through the fuel passage 70 into the plunger chamber 58 to thereby effect metering.

Both the check valves 92 and 94 are kept open until the metering is completed and the injection stroke commences. When both the check valves 92 and 94 are kept open, the piston chamber 56 and the plunger chamber 58 are kept at nearly the same pressure. Therefore, even if the booster piston 44 has moved more than the desired height of metering due to the pressure fluctuation within the piston chamber 56 and by the overshooting of the return spring 52 etc., the piston 44 can be returned against the fuel pressure in the plunger chamber 58 and can be stopped at a desired height of metering where the pressure within the piston chamber 56 is kept in equilibrium with the force of the return spring 52.

In the foregoing description, although only the rotary valve for one cylinder has been described for the convenience of explanation, if the number of cylinders increases, it is only necessary to form outlet ports equal in number to that of cylinders.

Figure 11:
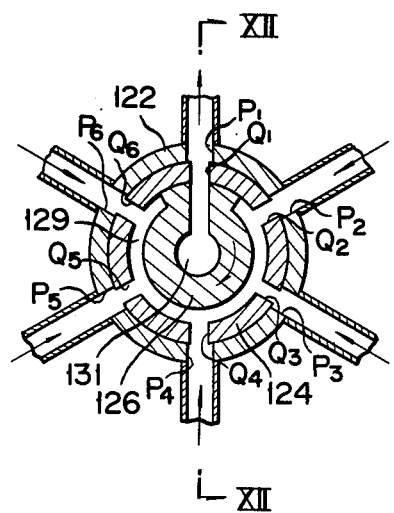
FIG. 11 is a sectional view of one embodiment of a rotary valve employed in the present invention, which is specifically adapted for a six-cylinder engine.
Figure 12:
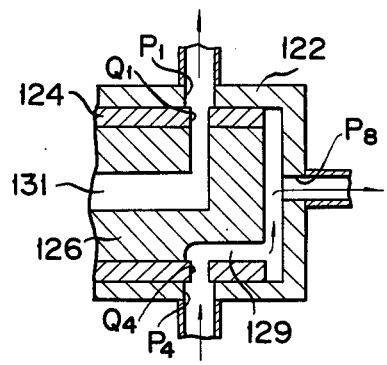
FIG. 12 is a sectional view taken along the line XII—XII of FIG. 11.

For example, rotary valve for 6-cylinder engine may be constructed as shown in FIGS. 11 and 12.

In FIGS. 11 and 12, housing 122 and rotary sleeve 124 are formed with six ports $P_1$ to $P_6$, $Q_1$ to $Q_6$, respectively. The ports $P_1$ to $P_6$ are connected to the injector (not shown) of each cylinder. Of course, each injector is constructed as shown in FIG. 2 or 10.

Whilst, the rotary shaft 126 has a recess 129 formed circumferentially in the lower outer peripheral part thereof, and a fuel passage 131 formed in the axial direction. One open end of this passage 131 is connected to the high pressure accumulator 16, and the other open end thereof opens in the outer peripheral part as shown and is adapted to communicate successively with the ports $Q_1$ to $Q_6$ of the rotary sleeve 124 as the rotary shaft 126 rotates. Further, the recess 129 of the rotary shaft 126 is arranged to communicate through the port $P_4$ of the housing 122 with the low pressure accumulator 42.

The fuel under high pressure introduced from the high pressure accumulator 16 into the passage 131 of the rotary shaft 126 is sent out through the ports $P_1$ to $P_6$ successively into each injector with the rotation of the rotary shaft 126. When one injector, for example, the injector connected to the port $P_1$ is injecting fuel into its associated cylinder, the injectors connected to other ports $P_2$ to $P_6$ are connected to the low pressure accumulator 42. Therefore, the back pressure of the booster pistons of the injectors connected to the ports $P_2$ to $P_6$ is kept at a pressure set by the low pressure accumulator 42 so that fuel in amount corresponding to the pressure in the piston chamber may be supplied into the plunger chamber of each injector. The fuel under high pressure is injected successively by the injectors connected to the ports $P_2$ to $P_6$ with the rotation of the rotary shaft 126.

Moreover, in the aforementioned embodiments, a motor is used as the rotary sleeve drive means 32 and the restrictor valve drive means 78, respectively, but they are not to be limited thereto; instead, a solenoid or pulse motor etc. may be employed.

As described hereinabove, according to the present invention, the fluctuation or changes in injection pressure due to the revolving speed of the engine can be eliminated and a stable and high injection pressure can be maintained in any range of revolution to ensure excellent fuel spraying condition so that the engine can be rotated always in good condition. Further, the correction of the injection timing and the amount of injection of fuel in proportion to the revolving speed of the engine provides excellent effects. Therefore the exhaust gas emission control, the noise control and the improvement of fuel combustion efficiency etc. can be dealt with readily.

It is to be understood that the foregoing description is merely illustrative of preferred embodiments of the invention, and that the scope of the invention is not to be limited thereto, but is to be determined by the scope of appended claims.

What we claim is:

1. A fuel injection system for an internal combustion engine having at least one cylinder and a cam shaft operatively associated therewith, comprising:
   a fuel pump driven by said engine for delivering fuel;
   first accumulator means for receiving and storing the fuel from said fuel pump;
   rotary valve means having an inlet port connected with said first accumulator means, at least one outlet port and a drain port, said rotary valve means comprising a housing, a sleeve mounted for rotation within said housing, said sleeve having at least one opening formed therein and rotary shaft means mounted for rotation within said sleeve, said rotary shaft means being rotated in synchronism with said cam shaft and having means for selectively connecting the outlet port with the inlet port and the drain port;
   means for automatically controlling position of said sleeve relative to said housing in response to number of revolutions of the engine;
   second accumulator means connected at one end with the drain port of said rotary valve means and at the other end with a tank;
   variable restrictor valve means disposed between said second accumulator means and said tank;
   means for automatically controlling degree of opening of said variable restrictor valve means in response to fluid pressure in said second accumulator means; and
   at least one injector means connected with the outlet port of said rotary valve means for injecting the fuel into said cylinder.

2. A fuel injection system as recited in claim 1 wherein said engine is multicylinder engine and wherein number of outlet ports formed in said rotary valve means and number of injectors correspond to number of cylinders of the engine.

3. A fuel injection system as recited in claim 2 wherein number of openings formed in said sleeve corresponds to number of cylinders of the engine and wherein the inlet port is formed in said rotary shaft means and the outlet ports and the drain port are formed in said housing.

4. A fuel injection system as recited in claim 1 further comprising means for connecting said first accumulator means with said second accumulator means.

5. A fuel injection system as recited in claim 1 wherein said injector means comprises;
   a body having a first, a second and a third bore formed therein, said body also having formed therein an inlet port, a drain port and a nozzle orifice communicated with the third bore;
   a piston slidably mounted in the first bore and defining a piston chamber therein;
   a plunger slidably mounted in the second bore with one end thereof contacting with said piston, said plunger together with said body defining a plunger chamber;
   a first passage for connecting the piston chamber with the plunger chamber;
   a needle valve slidably mounted in the third bore for opening and closing the nozzle orifice;
   a second passage for connecting the plunger chamber with the third bore;

metering means for introducing a metered amount of fuel into the plunger chamber; and means for communicating the third bore with the drain port of said injector means after injecting the fuel through the nozzle orifice thereby closing the nozzle orifice with said needle valve.

6. A fuel injection system as recited in claim 5 wherein said metering means comprises spring means for biasing said plunger towards increasing volume of the plunger chamber, means for connecting the piston chamber with said second accumulator means through said rotary valve means and means mounted in the first passage for allowing the fuel to flow from the piston chamber to the plunger chamber but blocking the opposite way.

7. A fuel injection system as recited in claim 6 wherein said last mentioned means comprises a single check valve.

8. A fuel injection system as recited in claim 6 wherein said last mentioned means comprises a first check valve mounted in the first passage at the side of the piston chamber, said first check valve having a spring mounted therein which is strong enough to allow the first check valve opened when the piston chamber is communicated with said second accumulator means but weak enough to allow the first check valve closed when the piston chamber is communicated with said first accumulator means, and second check valve mounted in the first passage at the side of the plunger for allowing the fuel to flow from the piston chamber to the plunger chamber but blocking the flow in the opposite direction.

9. A fuel injection system as recited in claim 5 wherein said communicating means comprises a passage formed in said plunger.

10. A fuel injection system as recited in claim 5 wherein said piston having formed therein means for communicating the first bore with the drain port of said injector means even when said piston is urged down and abuts a wall of said body defining the first bore opposite the piston chamber.

* * * * *